United States Patent
Yang et al.

(10) Patent No.: US 7,521,246 B2
(45) Date of Patent: Apr. 21, 2009

(54) CELL LYSIS BY HEATING-COOLING PROCESS THROUGH ENDOTHERMIC REACTION

(75) Inventors: Ji-yeon Yang, Seongnam-si (KR);
Yoon-kyoung Cho, Suwon-si (KR);
Jin-tae Kim, Hwaseong-si (KR);
Sook-young Kim, Yongin-si (KR);
Young-sun Lee, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 170 days.

(21) Appl. No.: 11/335,414

(22) Filed: Jan. 19, 2006

(65) Prior Publication Data

US 2006/0258012 A1 Nov. 16, 2006

(30) Foreign Application Priority Data

Jan. 20, 2005 (KR) .................. 10-2005-0005537

(51) Int. Cl.
*G01N 33/48* (2006.01)
(52) U.S. Cl. .................. 436/63; 436/147; 436/174; 422/68.1; 422/82.12; 435/4; 435/29
(58) Field of Classification Search .................. 436/63, 436/147, 174, 177; 422/68.1, 82.12, 61, 422/101; 435/4, 29
See application file for complete search history.

(56) References Cited

U.S. PATENT DOCUMENTS

| 3,804,077 | A | * | 4/1974 | Williams | 126/263.1 |
| 4,751,119 | A | * | 6/1988 | Yukawa | 428/34.4 |
| 5,270,183 | A | * | 12/1993 | Corbett et al. | 435/91.2 |
| 6,248,257 | B1 | | 6/2001 | Bell et al. | |
| 6,672,458 | B2 | * | 1/2004 | Hansen et al. | 209/224 |
| 2002/0142482 | A1 | | 10/2002 | Wu et al. | |
| 2006/0115873 | A1 | * | 6/2006 | Peak et al. | 435/41 |

FOREIGN PATENT DOCUMENTS

| EP | 149514 | * | 7/1985 |
| EP | 0637998 B1 | | 7/1996 |
| EP | 0637966 B1 | | 7/1997 |
| KR | 1020010035352 A | | 5/2001 |

OTHER PUBLICATIONS

He, Y. et al. "Integrated electroosmotically-driven on-line sample purification system for nanoliter DNA sequencing by capillary electrophoresis" J. Chrom. A 894 (2000): 179-190.
He, Y. et al. "Capillary-based fully integrated and automated system for nanoliter polymerase chain reaction analysis directly from cheek cells" J. Chrom. A 924(2001) 271-284.
"Calcium Oxide", Hawley's Condensed Chemical Dictionary, 14th Edition, John Wiley & Sons, Inc., 2002.
Clugston MJ et al. Advanced Chemistry, 2000, ISBN 0199146330, Oxford University Press, p. 287.

* cited by examiner

*Primary Examiner*—Maureen M Wallenhorst
(74) *Attorney, Agent, or Firm*—Cantor Colburn LLP

(57) ABSTRACT

Provided is a cell lysis method including: preparing a cell sample to be lysed; heating the cell sample; and cooling the cell sample by causing an endothermic reaction near the cell sample. According to the method, cell lysis can be simply and conveniently performed without regard to location and without additional devices since a separate energy source is not required and the apparatus is portable. In particular, when cell lysis is performed in a biochip using a small amount of sample, a greater cell lysis effect can be obtained. In addition, cell lysis efficiency is significantly improved, compared to when only heating is performed.

10 Claims, 5 Drawing Sheets

CELL LYSIS BY HEATING-COOLING PROCESS THROUGH ENDOTHERMIC REACTION

BACKGROUND OF THE INVENTION

This application claims the benefit of Korean Patent Application No. 10-2005-0005537, filed on Jan. 20, 2005, in the Korean Intellectual Property Office, the disclosure of which is incorporated herein in its entirety by reference.

1. Field of the Invention

The present invention relates to a cell lysis method using temperature variation, and more particularly, to a method of lysing cells using temperature variation through repeated cooling and heating processes, in which an endothermic reaction is used to cause temperature variations, which is convenient to perform and reduces time and costs.

2. Description of the Related Art

Cell lysis is a process of releasing materials in a cell by disrupting the cell membrane, and in particular, a process of extracting intracellular materials from a cell to isolate DNA or RNA before amplification, such as a polymerase chain reaction (PCR).

Cell lysis methods through cell rupture can be classified into mechanical methods and non-mechanical methods.

Mechanical methods include ultrasonication, disruption using a homogenizer, pressing using, for example, a French press, etc., decompression, pulverization, etc. Non-mechanical methods include chemical methods, thermal methods, enzymatic methods, etc.

For example, conventional ultrasonication, which is a mechanical method, is performed on cell solution and suspension in a chamber located in an ultrasonic bath. Such ultrasonic disruption leads to many disadvantages in cell lysis. First, a nonuniform ultrasonic energy distribution causes inconsistent results. Second, the ultrasonic bath cannot concentrate on the chamber, and thus, a large amount of time is required to complete cell disruption.

Chemical methods, which are non-mechanical methods, use, for example, an acid, a base, a detergent, a solvent, a chaotropic reagent, etc. Especially, a chemical method using a detergent is widely used. Detergents disrupt a lipid double membrane to release cell contents and lyses membrane protein. Detergents are most commonly used to lyse animal cells. Most detergents denature protein. However, a reagent for cell lysis should be separately added, and hence a subsequent process of removing the reagent is required. PCR inhibition may occurs, and the process takes a long time.

Enzymatic methods use lysozyme, protease, etc.

Thermal methods include freezing-thawing, heating, osmotic impact, electric impact, etc. For example, cell lysis is achieved by contacting cells with a hot object, such as a hot plate, or by repeating a cycle of freezing to −70° C. and thawing to room temperature.

A cell lysis method using heat, which is neither a mechanical method nor uses a reagent, is suitable to be used in a lab-on-a-chip (LOC). In particular, the freezing-thawing method is known to be more efficient to lyse cells than a simple heating method. However, an expensive rapid cooling apparatus for cooling to −70° C. is required and it takes a long time. Further, when a small amount of a sample is used as in a LOC, the moisture in the sample easily vaporizes and the sample easily dries. In addition, this method causes protein denaturation, which inhibits PCR. These problems also arise with simple heating methods.

In particular, when cell lysing gram positive bacteria, it is difficult to obtain a desired cell lysis effect only using a conventional heating method.

Thus, the inventors performed intensive research in order to discover a cell lysis method of repeating cooling and heating processes that does not require a separate expensive apparatus, can be used regardless of time and place, is simple and convenient to perform, and does not inhibit PCR, and completed the present invention.

SUMMARY OF THE INVENTION

The present invention provides an efficient cell lysis method using an endothermic reaction occurring in a cooling-heating process. The method can be easily used in a lap-on-a-chip (LOC) without regard to location and without additional devices.

The present invention provides a portable cell lysis apparatus realizing the cell lysis method.

According to an aspect of the present invention, there is provided a cell lysis method including: preparing a cell sample to be lysed; heating the cell sample; and cooling the cell sample by causing an endothermic reaction near the cell sample.

In the method, the heating and the cooling may be repeated at least twice.

In the method, the heating may be performed using any method, for example, using heat generated during the exothermic reaction. The heating temperature may be 90° C. or higher and 100° C. or lower, and the cooling temperature may be as low as possible, for example, 30° C. or lower and −30° C. or higher.

According to another aspect of the present invention, there is provided a cell lysis apparatus including: a heating portion; a cooling portion; and a sample containing channel which alternately passes through the heating portion and the cooling portion at least one time.

In the cell lysis apparatus, the heating portion may include any heating element without limitation. For example, the heating portion may contain at least one material capable of inducing an exothermic reaction by being mixed together.

In the cell lysis apparatus, the cooling portion may include any cooling element without limitation. For example, the cooling portion may contain at least one material capable of inducing an endothermic reaction by being mixed together.

In the cell lysis apparatus, the sample containing channel may have a sample inlet and a sample outlet. In this case, the sample outlet may be connected to a PCR chamber.

The size and the shape of the cell lysis apparatus are not limited. However, the cell lysis apparatus may be in the form of a portable package.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail.

A cell lysis method according to an embodiment of the present invention includes: preparing a cell sample to be lysed; heating the cell sample; and cooling the cell sample by causing an endothermic reaction around the cell sample.

Any cell can be lysed according to the present invention without limitation. The kinds of cell samples that can be used in the present invention include a cell suspension containing microorganism strains, a sample including somatic cells of human, etc. The cell lysis method according to the present invention is proved to be effective in cell lysing gram positive bacteria, such as *Bacillus substilus, Bacillus Megatrium*, etc., which cannot be easily lysed by a general heating method.

In the cell lysis method according to the present invention, at least one cycle of alternate heating and cooling is repeated.

In the present invention, a heating process may be performed using any method for increasing the temperature of cells, for example, an electrical method, a chemical method, a physical method and so on, to which the present invention is not limited. The heating method may be properly selected by those skilled in the art according to the form of the cell sample and the characteristics of a reaction vessel.

For convenience and portability, the heating process may be performed using heat generated during an exothermic reaction. The exothermic reaction refers to a reaction generating heat when reactants are chemically reacted to obtain products. Any reaction satisfying this requirement may be used. Examples of the exothermic reaction that can be used in the present embodiment are as follows.

There are an exothermic reaction in which heat is generated by reacting $MgSO_4$, NaOH or CaO with water, an exothermic reaction in which heat is generated by adding sulfuric acid to a solid including CaO and $MgCl_2$ or $MgSO_4$ and NaOH, an exothermic reaction in which heat is generated by reacting CaO with a $MgCl_2$ solution, an exothermic reaction in which heat is generated by reacting CaO with a strong acid (e.g., HCl and $H_2SO_4$). In addition, there are an exothermic reaction in which heat is generated by reacting CaO with phosphorous or a phosphate compound, an exothermic reaction in which heat is generated by contacting a solid including CaO, $AlCl_3$, NaOH and Al with a liquid including NaCl, $CaCl_2$, $MgCl_2$, $NH_4Cl$ or $Fe(NO_3)_3$, an exothermic reaction which CaO is reacted with sulfuric acid, an exothermic reaction in which CaO, $MgCl_2$ and NaOH are reacted with sulfuric acid, etc.

In an exemplary embodiment of the present invention, at least one reaction compound that can induce an exothermic reaction as described above is put into separate containers, such as plastic bags, tubes, microcapsules, or other containers not to be mixed with each other, and then the containers are packed in one package. Thereafter, when performing cell lysis, external impact or other stimulus is applied to the bags, tubes, microcapsules, etc. to burst the containers so that the separated compounds are mixed with each other and cause an exothermic reaction. The temperature of the cell sample is increased due to the heat generated during the exothermic reaction.

The cooling process is performed using an endothermic reaction in a similar manner to the above-described heating process. The endothermic reaction refers to a chemical reaction in which ambient heat is absorbed when reactants are chemically reacted to obtain products. Any reaction satisfying this requirement may be used in the present invention without limitation. Examples of the endothermic reaction are as follows.

$$2NH_4NO_3 (s) + H_2O (l) + heat \rightarrow NH_4^+(aq) + NO_3^-(aq)$$

$$Ba(OH)_2\ 8H_2O (s) + 2NH_4NO_3 (s) \rightarrow Ba(NO_3)_2 (s) + 2NH_3(aq) + 10H_2O(l)$$

In the present invention, heat resulting from the exothermic reaction during the heating process initiates an endothermic reaction. Similar to the exothermic reaction, in an embodiment of the present invention, at least one reaction compound which can cause an endothermic reaction are put into separate containers, such as plastic bags, tubes, microcapsules, or other containers, not to be mixed with each other, and then the separated compounds are packed in one package. Thereafter, when performing cell lysis, external impact or other stimulus is applied to the bags, tubes, microcapsules, etc. to burst the containers so that the separated compounds are mixed with each other and cause an exothermic reaction. The temperature of the sample is decreased due to heat absorption during the endothermic reaction.

In the method of the present embodiment, the heating temperature and the heating time, and the cooling temperature and the cooling time may be properly selected by those skilled in the art according to the cell sample to be lysed and a desired degree of cell lysis. In general, the heating temperature may be 90° C. or higher, and the cooling temperature may be lower than 30° C., preferably sub-zero temperature More preferably, the heating temperature may be 90° C. or higher and lower than 100° C., and the cooling temperature may be lower than 30° C. and –30° C. or higher. Rapid cooling at a temperature as low as possible is preferred. If the heating temperature is not 90° C. or higher, it is difficult to obtain a desired cell lysis result. If the cooling temperature is not lower than 30° C., there is no different effect from when only the heating process is performed.

According to the present invention, at least one cycle of alternate heating and cooling processes are performed on a cell sample. As described in examples below, the larger the number of heating and cooling processes, the higher the cell lysis efficiency.

In an embodiment of the cell lysis method according to the present invention, a chip-type cell sample is alternately subjected to the heating process and the cooling process. In detail, for example, the chip-type cell sample is exposed to an exothermic reaction and then to an endothermic reaction after a predetermined time. These processes are repeated to lyse the cell. In this case, the cell sample may undergo temperature variations by being placed in a heating pack in which an exothermic reaction occurs and then in a cooling pack in which an endothermic reaction occurs.

The cell lysis method according to the present invention can be implemented using any apparatus, for example, a cell lysis apparatus including a heating portion, a cooling portion, and a sample containing channel which alternately passes through the heating portion and the cooling portion at least one time.

In the cell lysis apparatus, the heating portion may contain at least one material capable of leading to an exothermic reaction by being mixed together, and the cooling portion may contains at least one material capable of leading to an endothermic reaction by being mixed together.

The sample containing channel may have a sample inlet and a sample outlet. The sample outlet may be connected to a PCR chamber.

Figure 1:
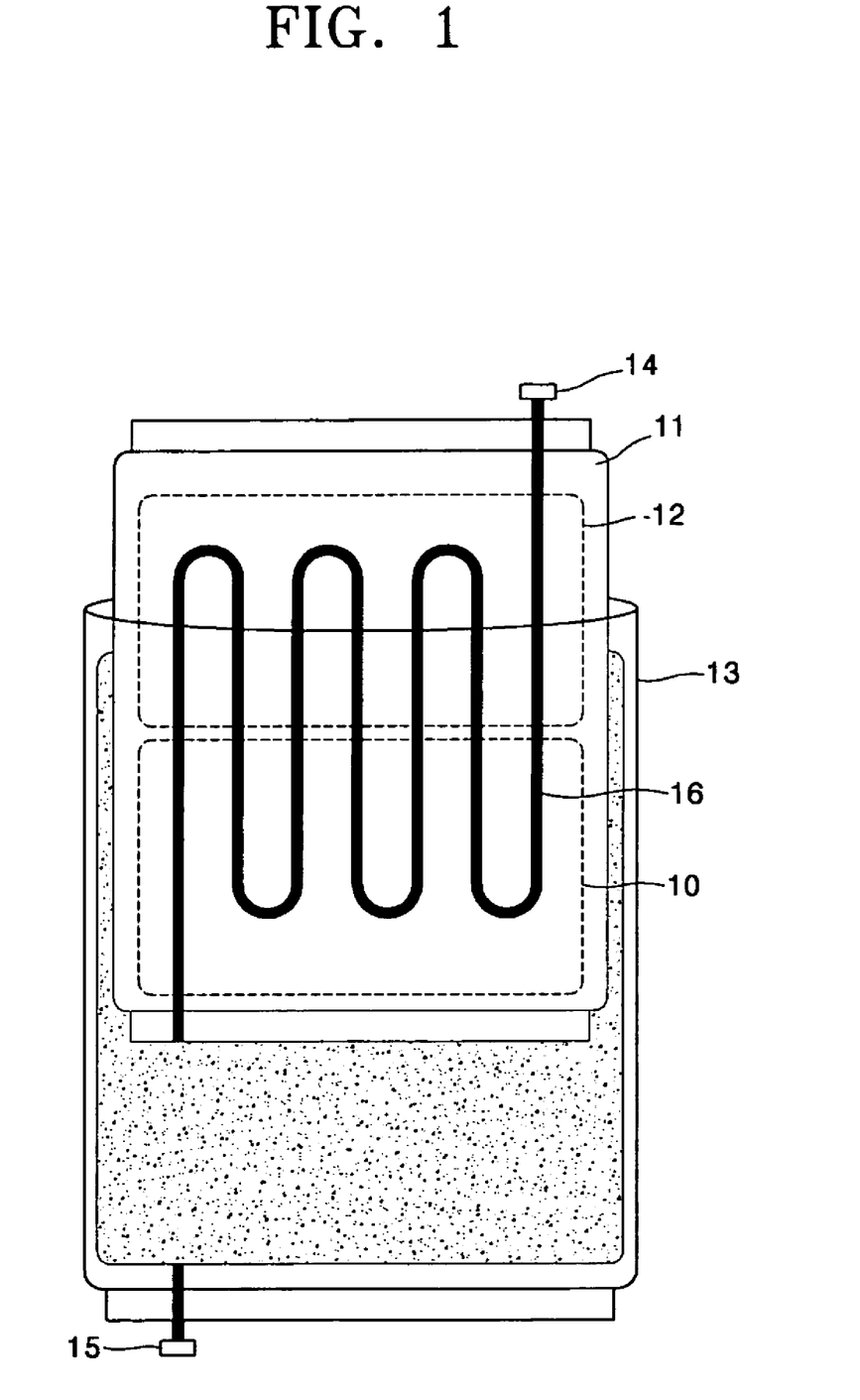
FIG. 1 is a schematic diagram of a cell lysis apparatus according to an embodiment of the present invention.

A cell lysis apparatus according to an embodiment of the present invention is illustrated in FIG. 1. The present invention will now be described in greater detail with reference to FIG. 1.

The cell lysis apparatus in FIG. 1 is of a pack type, which is easy to carry. The cell lysis apparatus includes an outer pack 13 and an inner pack 11. The inner pack 11 includes a heating pack 12 and a cooling pack 10. A sample containing channel 16 in which a cell sample is present is included in the inner pack 11. The sample containing channel 16 may be a zigzag-shaped pipe as illustrated in FIG. 1. The sample containing channel 16 alternately passes through the heating pack 12 and the cooling pack 10. The sample containing channel 16 may contact the surface of the inner pack 11 or may be inserted into the inner pack 11. The sample containing channel 16 may be composed of any material which is commonly used in the art. For example, the sample containing channel 16 can be a chip, a capillary, tube, a microchannel, etc. which are composed of silicon, glass, plastic, etc.

A cell sample is injected into the sample containing channel 16 through a sample inlet 14, which may have a cap, and flows along the sample containing channel 16 while alternately passing through the cooling portion and the heating portion, thereby causing cell lysis. The resulting cell lysate flows along the sample containing channel 16 to a sample outlet 15, which may have a cap. The cell lysate is discharged through the sample outlet 15. The discharged cell lysate can be used in a subsequent process. For example, the sample outlet 15 may be connected to a reaction vessel for flow-through PCR or any conventional PCR vessel (not shown).

As described above, the sample containing channel 16 may have the sample inlet 14 and the sample outlet 15. The sample outlet 15 may be provided near the heating pack 12 or the cooling pack 10.

Figure 2A:
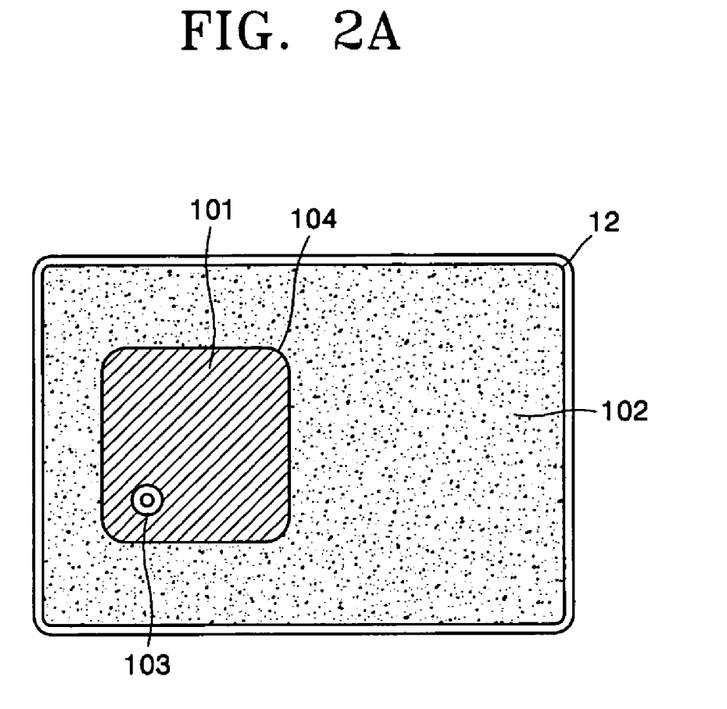
FIGS. 2A and 2B are schematic diagrams of a heating pack and a cooling pack, respectively, of the cell lysis apparatus illustrated in FIG. 1
Figure 2B:
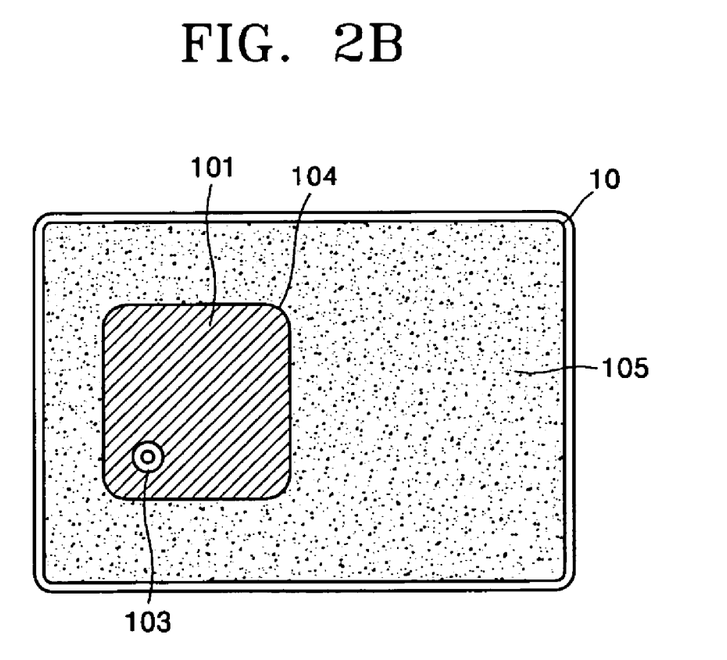

The heating pack 12 and the cooling pack 10 are illustrated in greater detail in FIGS. 2A and 2B.

Referring to FIG. 2A, the heating pack 12 may further include a reactant pack 104 for separating reactants. In an embodiment of the present invention, the reactant pack 104 contains water, and a space outside the reactant pack 104 contains a compound 102 which can react with water to induce an exothermic reaction. When an element 103, which can be a button, for tearing the reactant pack 104 is touched to tear the reactant pack 104 for cell lysis, the water in the reactant pack 104 flows out and undergoes an exothermic reaction with the compound 102, thereby generating heat. This heat increases the temperature of the cell sample. This process may be performed in any manner as long as it involves tearing a bag, tube or microcapsule by external impact or other stimuli to allow the reactants, which are separated from each other, to be mixed to cause an exothermic reaction.

FIG. 2B illustrates the cooling pack 10 in greater detail. The cooling pack 10 has the same structure as the heating pack 12, except that a space outside the reactant pack 104 contains a compound 103 which can react with water to induce an endothermic reaction. In the cooling pack 10, an endothermic reaction is induced in the same manner as in the heating pack 12, thereby decreasing the temperature of the cell sample.

A cell lysis apparatus according to an embodiment of the present invention may be a portable form which does not require a separate energy source, as illustrated in FIG. 1. Also, a cell lysis apparatus according to an embodiment of the present invention may further include an electrical heating element in the heating portion.

The present invention will now be described in greater detail with reference to the following examples. The following examples are for illustrative purposes only and are not intended to limit the scope of the invention.

EXAMPLE 1

Formation of a Heating Pack

The heating pack 12 in FIG. 1 was formed using 2 g of a solid composition containing 5 wt % of MgCl and 6 wt % of NaOH with respect to 100 wt % of CaO and 5 ml of water. The heating pack 12 was composed of glass.

An external impact was applied to the heating pack 12 to induce an exothermic reaction in the heating pack 12. At this time, the temperature of the heating pack 12 increased up to 90° C., which was maintained for 10 min.

Formation of a Cooling Pack

The cooling pack 10 in FIG. 1 was formed using water and ammonium nitrate ($NH_4NO_3$) which can induce an endothermic reaction by being mixed together. The cooling pack 10 was composed of glass.

Figure 3:
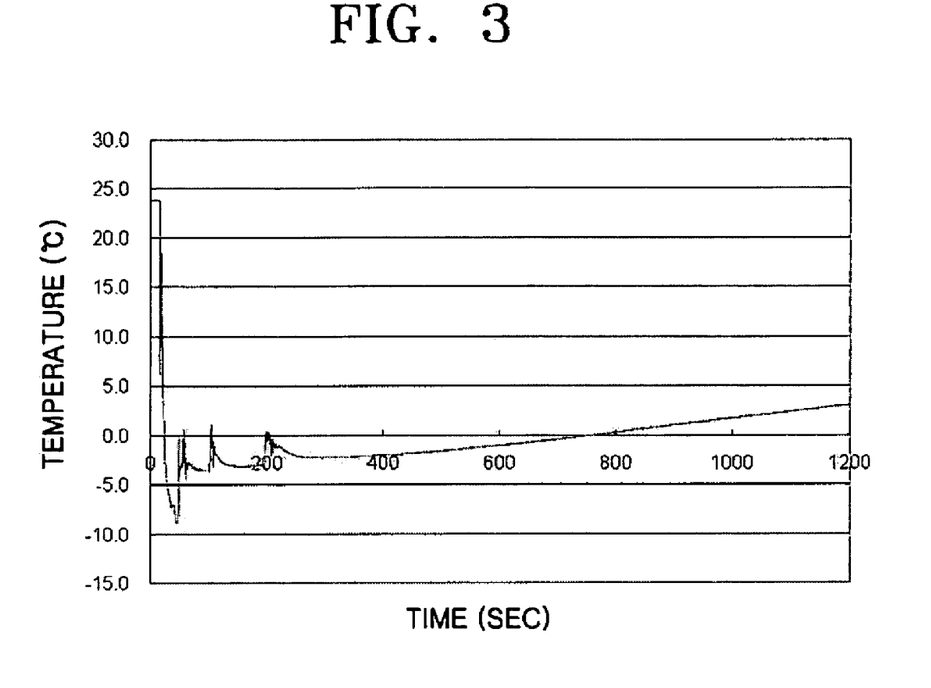
FIGS. 3 and 4 are graphs of temperature versus time produced during an endothermic reaction.

In the cooling pack 10, 80 g of solid ammonium nitrate and 9 ml of water were used to cause an endothermic reaction. The temperature of the cooling pack 10 was measured. The results are shown in FIG. 3. It can be seen from FIG. 3 that when an endothermic reaction occurs between ammonium nitrate and water, the temperature below zero is maintained for 10 min or longer.

Alternately, a temperature drop resulting from endothermic reaction was measured using ammonium nitrate and solid hydrous barium hydroxide ($Ba(OH)_2 \cdot 8H_2O$) in the same manner as described above.

Figure 4:
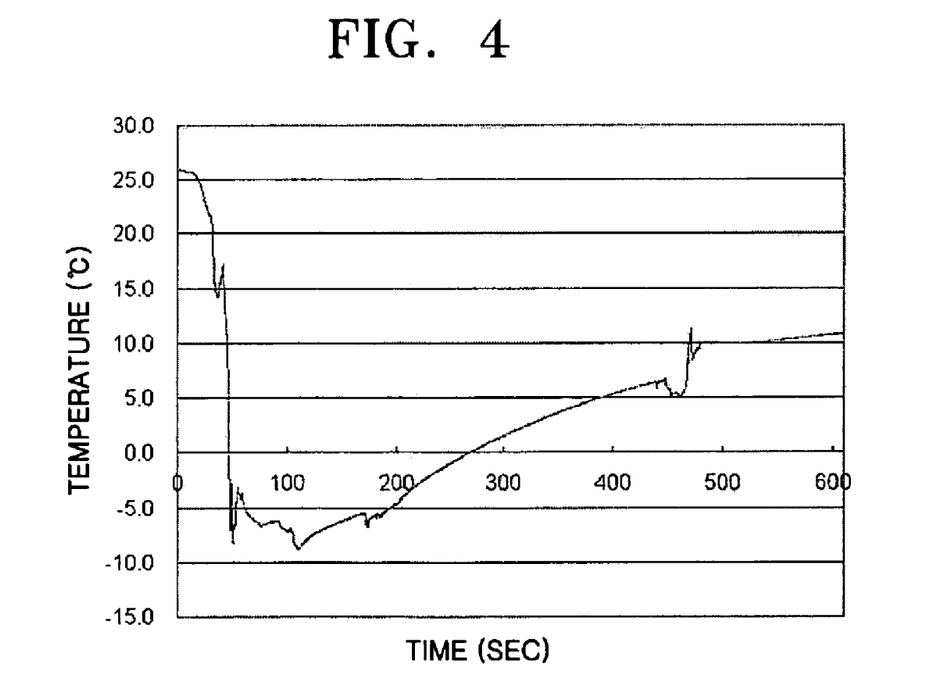

5 g of solid ammonium nitrate and 10 g of solid hydrous barium hydroxide were used to cause an endothermic reaction. The temperature was measured. The results are shown in FIG. 4. As can be seen from FIG. 4, the temperature was reduced to a lower level than when ammonium nitrate and water were used, but the temperature was maintained for a shorter duration.

The cell lysis method according to the present invention can be implemented using a suitable endothermic reaction, which can be selected from known endothermic reactions depending on the type of cell sample to be used.

Fabrication of a Cell Lysis Apparatus

As illustrated in FIG. 1, the heating pack 12 and the cooling pack 10 were fabricated, and then the tube 16 through which the cell sample could pass was formed. The tube 16 was a microchannel composed of silicone with a diameter of about 100 μm. Subsequently, the tube 16 was fixed to contact both of the heating pack 12 and the cooling pack 10, thereby fabricating the cell lysis apparatus (see FIG. 1).

EXAMPLE 2

Cell lysis was performed on gram positive bacteria *B. megatrium* and gram negative bacteria *E. coli*, respectively, as described below, and the results were identified using PCR.

Preparation of a Cell Sample

100 μl of a cell sample source was inoculated into 5 ml of a LB medium and cultured for about 20 hours, and then dispensed into 5 e-tube vials. After centrifugation at 13.2 rpm for 3 minutes, the supernatant was discarded and the remainder was washed with distilled water. Centrifugation was performed at 13.2 rpm for 0.5 minute, and the supernatant was discarded. Each vial was resuspended with distilled water. Samples were collected in a 15 ml Falcon tube (total 5 ml).

The cell sample was diluted to 1/10 and measured with UV spectrum (600 nm). Assuming that *B. megatrium* has 1 copy of DNA per a cell and HBV of *E. coli* has 10 copies of HBV plasmid DNA per a cell, an initial cell concentration based on DNA, which was calculated using the measured UV spectrum value, was $10^9$ DNA/μl Cell samples having two different concentrations were prepared based on the initial cell concentration and used in the following test. That is, HBV of *E. coli* having concentrations of $10^6$ DNA/μl and $10^4$ DNA/μl and *B. magatrium* having concentrations of $10^5$ DNA/μl and $10^3$ DNA/μl were tested as follows (see FIGS. 5 through 7).

Cell Lysis

A PCR solution was prepared as follows:

1×SYBR Green PCR buffer (PE Biosystems), 1 mM of forward primer and reverse primer (Genotech, Korea), each 200 uM dNTP (deoxynucleoside triphosphates) (Sigma), 5 mM $MgCl_2$ (Sigma), 5% glycerol (Sigma), 500 mM formamide (Promega), 0.2 ng/μl BSA (Sigma), 1.1 unit/μl uracil-N-glycosylase (Sigma), 0.1 unit/μl Taq polymerase (SolGent. Co., Ltd, Korea).

5 μl of the PCR solution and 5 μl of the cell sample were mixed. 1.1 μl of the mixture was injected into a silicon micro PCR chip. Cell lysis was induced while varying temperature according to the method of the present invention. That is, for each of *B. megatrium* and *E. coli*, control tests in which samples were only heated at 95° C. for 1 min and for 3 min were performed, and experiments in which samples underwent a cycle of heating at 95° C. for 1 min and cooling at −20° C. for 2 min one time and three times. The resultant from the experiments was used in the following PCR.

PCR

A PCR was performed on the resultant from the cell lysis using a real-time PCR device GenSpector® TMC-1000 (available from Samsung Electronics Co., Ltd.) with a silicon-glass binding chip under the following conditions.

```
For B. megatrium, the following 16S rRNA primer
was used.
PAI-1F:
5'-YCCAKACTCCATACGGGAGGC-3' (SEQ ID No: 1)
(Tm 69.1° C.)

PAI-1R:
5'-GATTTACCGCRRCTGGCAC-3' (SEQ ID No: 2)
(Tm 58.8° C.)
```

```
-continued
In the case of HBV of E. coli, the following
primer was used.
TMP5-F:
5'-AGTGTGGATTCGCACTCCT-3' (SEQ ID No: 3)
(Tm 54° C.)

TMP5-R:
5'-GAGTTCTTCTTCTAGGGGACCTG-3' (SEQ ID No: 4)
(Tm 56° C.)
```

Using the primers, PCR was performed by predenaturing at 50° C. for 10 min and at 91° C. for 2 min and 50 cycles of amplification at 92° C. for 1 sec and at 65° C. for 15 sec. The melting temperature (Tm) was identified while increasing the temperature of the resulting PCR product from 60° C. to 90° C. at a rate of 0.1° C./sec. The Tm was 77° C., indicating that intact PCR products were obtained.

Figure 5:
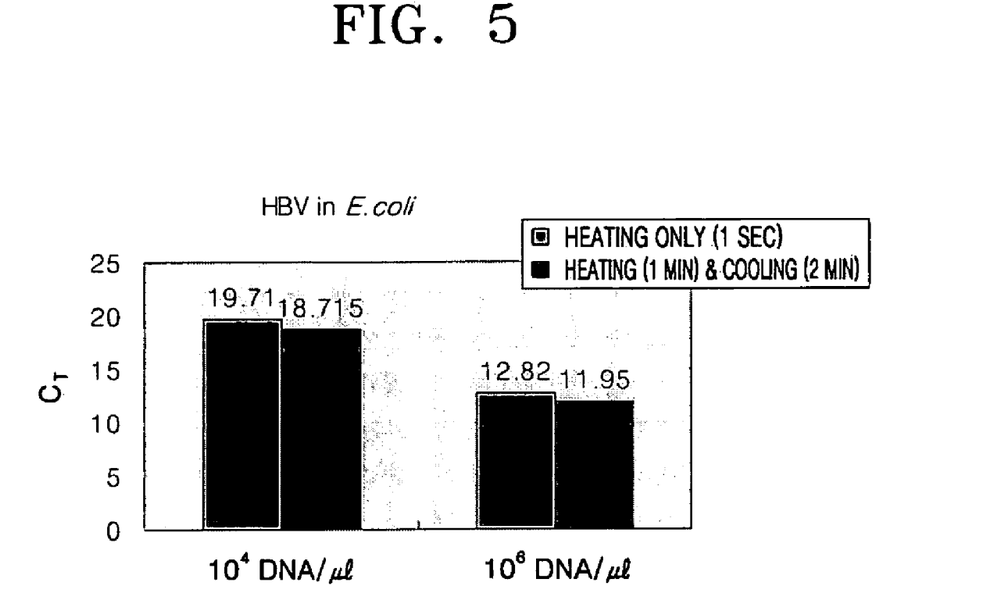
FIG. 5 illustrates $C_T$ values of *E. coli* samples after a polymerase chain reaction (PCR) following cell lysis by simple heating and a cell lysis method according to the present invention.
Figure 6:
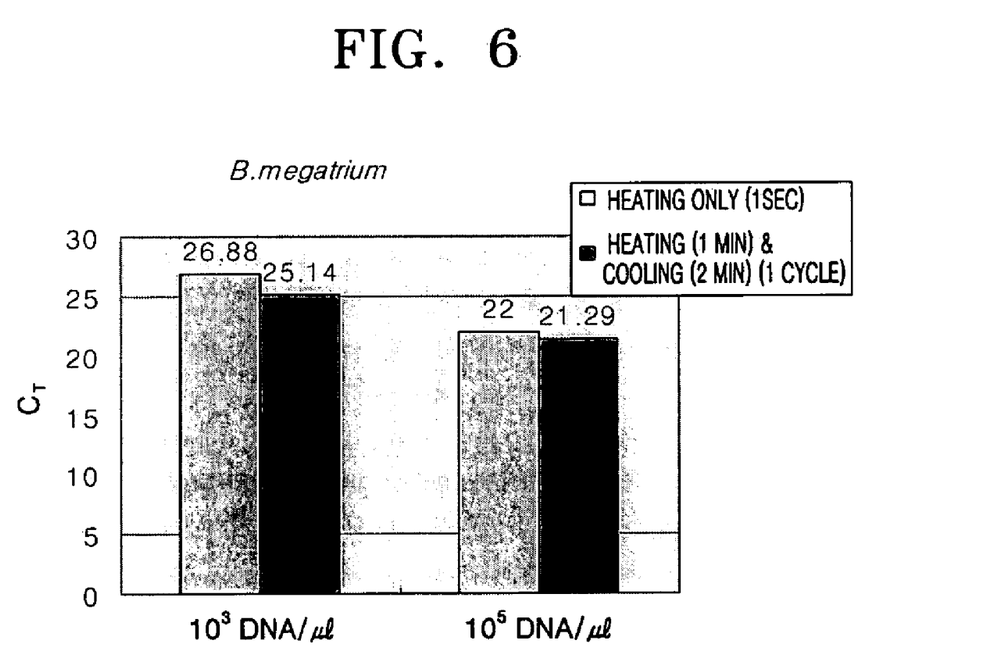
FIGS. 6 and 7 illustrate $C_T$ values of *B. megatrium* samples after a PCR following cell lysis at various temperatures and times.
Figure 7:
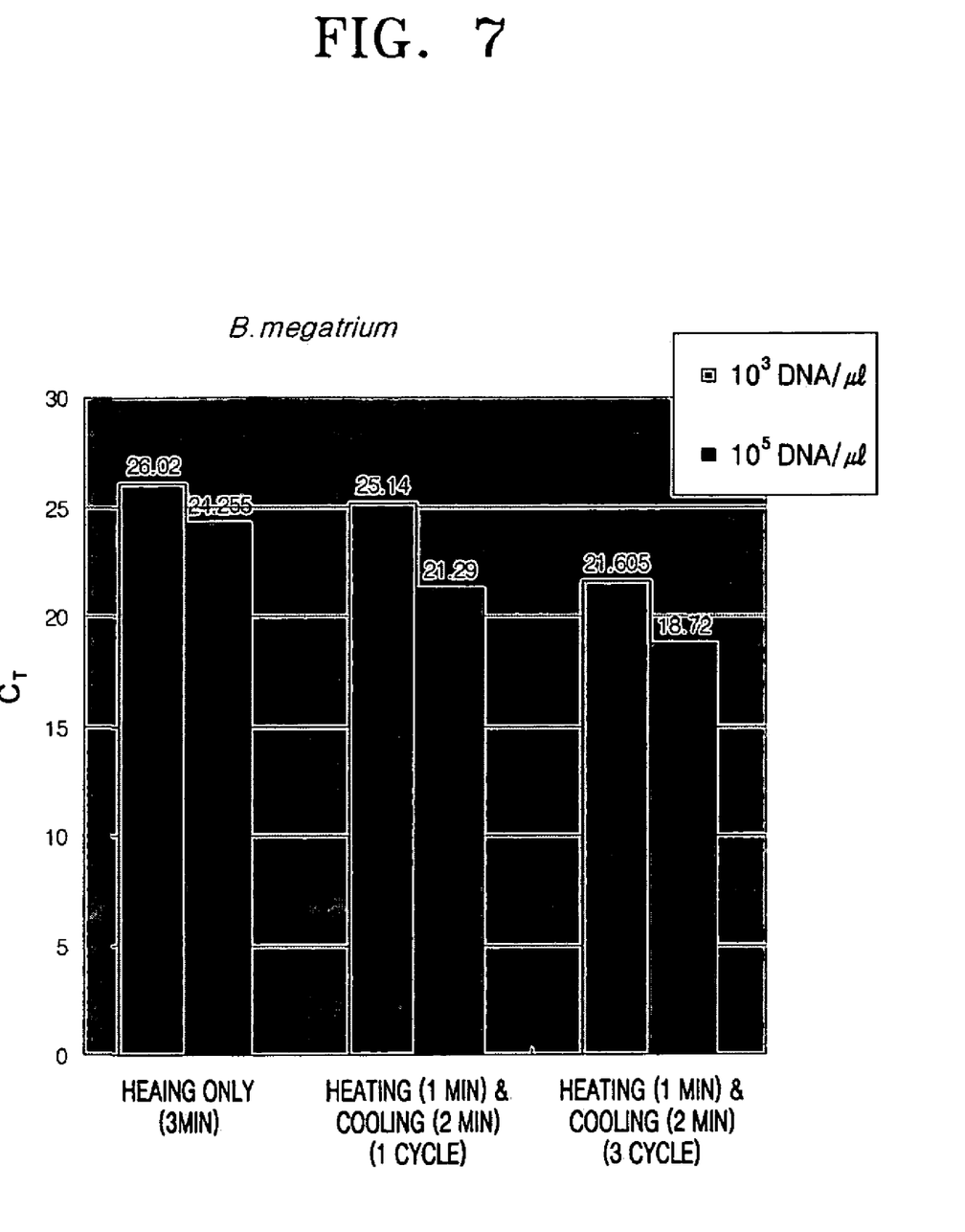

The DNA concentration of the obtained PCR product and the initial DNA concentration were used to identify a $C_T$ value, thereby verifying a cell lysis effect in each sample. The results are illustrated in FIGS. 5 through 7. The intensity of fluorescent signals in real-time PCR increases depending on the amount of PCR products. $C_T$ represents the number of cycles leading to a threshold fluorescent value. It is known that $C_T$ is associated with the initial DNA concentration and a difference of 3.3 cycles in $C_T$ corresponds to a difference of 10 times in the initial concentration.

As can be seen from FIGS. 5 through 7, the $C_T$ value of the sample which was simply heated for a time duration was greater than that of the sample on which heating and cooling were repeatedly performed, indicating that the latter sample had a significantly great cell lysis effect. FIG. 7 shows that when the number of heating-cooling cycles increases, the cell lysis effect further increases.

In particular, a good cell lysis effect even on gram positive bacteria, such as *B. megatrium*, which is not easily lysed using the conventional method, can be obtained.

In a method and apparatus for cell lysis according to the present invention, cell lysis can be simply and conveniently performed without regard to location and without additional devices since a separate energy source is not required and the apparatus is portable. In particular, when cell lysis is performed in a biochip using a small amount of sample, a greater cell lysis effect can be obtained. In addition, cell lysis efficiency is significantly improved, compared to when only heating is performed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cell lysis method comprising:
   heating a cell sample to be lysed; and
   cooling the cell sample by causing an endothermic reaction near the cell sample;
   wherein heating and cooling are repeated at least twice; and
   wherein heating and cooling result in lysis of the cells in the cell sample.

2. The cell lysis method of claim 1, wherein the heating is performed using heat generated during an exothermic reaction.

3. The cell lysis method of claim 1, wherein the heating is performed at a temperature of 90° C. or higher and 100° C. or lower, and the cooling is performed at a temperature of 30° C. or lower and −30° C. or higher.

4. The cell lysis method of claim 1, wherein the endothermic reaction is a reaction between $NH_4NO_3$ (s) and $H_2O$(l) or a reaction of $Ba(OH)_2 8H_2O$ (s) and $NH_4NO_3$ (s).

5. A cell lysis apparatus comprising:
   a heating portion, wherein the heating portion contains a solid material consisting of 5 to 7 wt % of $MgCl_2$ or $MgSO_4$ and 5 to 7 wt % to of NaOH with respect to 100 wt % of CaO to induce an exothermic reaction;
   a cooling portion; and
   a sample containing channel which alternately passes through the heating portion and the cooling portion at least one time.

6. The cell lysis apparatus of claim 5, wherein the cooling portion contains at least two materials capable of inducing an endothermic reaction by being mixed together.

7. The cell lysis apparatus of claim 6, wherein the at least two materials include $NH_4NO_3$ or $Ba(OH)_2 8H_2O$.

8. The cell lysis apparatus of claim 5, wherein the sample containing channel has a sample inlet and a sample outlet.

9. The cell lysis apparatus of claim 8, wherein the sample outlet is connected to a PCR chamber.

10. The cell lysis apparatus of claim 5, being in the form of a portable package.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
```

```
-continued yccakactcc atacgggagg c                                              21

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
gatttaccgc rrctggcac                                                 19

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
agtgtggatt cgcactcct                                                 19

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gagttcttct tctaggggac ctg                                            23
```